United States Patent
Hollars (10) Patent No.: US 6,843,388 B1
(45) Date of Patent: Jan. 18, 2005

(54) COMPRESSED GAS CARTRIDGE DISPENSING SYSTEM ALLOWING INTERCHANGEABLE USE OF DIFFERENT CAPACITY COMPRESSED GAS CARTRIDGES AND NOVEL STORAGE FEATURE

(76) Inventor: Anthony Scott Hollars, 6445 W. Lost Canyon Dr., Tucson, AZ (US) 85745

(*) Notice: Subject to any disclaimer, the term of this patent is extended or adjusted under 35 U.S.C. 154(b) by 67 days.

(21) Appl. No.: 10/199,281

(22) Filed: Jul. 22, 2002

(51) Int. Cl.$^7$ .............................................. B67D 5/00
(52) U.S. Cl. .............................. 222/5; 222/83; 222/91; 222/183
(58) Field of Search ........................ 222/3, 5, 83, 91, 222/183

(56) References Cited

U.S. PATENT DOCUMENTS

| | | | |
|---|---|---|---|
| 3,269,598 A | * | 8/1966 | Butters et al. .................. 222/5 |
| 3,361,298 A | * | 1/1968 | Trumble ......................... 222/5 |
| 3,579,964 A | * | 5/1971 | Ohlstein ......................... 222/5 |
| 4,498,605 A | * | 2/1985 | Mackal et al. .................. 222/5 |
| 5,076,468 A | * | 12/1991 | Mackal ........................... 222/5 |
| 5,544,670 A | | 8/1996 | Phillips et al. |
| 6,220,274 B1 | * | 4/2001 | Wang ........................ 137/231 |
| 6,601,731 B2 | * | 8/2003 | Wu ................................ 222/5 |

OTHER PUBLICATIONS

Catalog, Innovations in Cycling, Inc. 2001/2002 front cover, pp. 1–3, 8, Tucson, Arizona, USA.
SKS Metaplast GmbH of Germany, front and rear copies of dispenser s retail packaging and one copy of dispenser as disclosed on SKS Web page circa Jul., 2002.
isi Industrial Products gas cylinder product literature, six (6) pages total, particularly Product Information Table on p. 3.

\* cited by examiner

Primary Examiner—Joseph A. Kaufman
(74) Attorney, Agent, or Firm—John D. Lister; J. Marc Edwards (57) ABSTRACT

A compressed gas cartridge dispensing system capable of dispensing at least two different capacities of non-threaded neck compressed gas cartridges as well as optionally dispensing all cartridges having a ⅜-24 neck thread. The standard 12-gram $CO_2$ non-threaded neck compressed gas cartridge fits this dispenser. The same dispensing system is also capable of dispensing larger capacity cartridges having a neck dimensioned smaller than a ⅜-24 female thread minor diameter with a water capacity in the range of 16 to 50 ml. Obvious advantages to the dispensing system are added options offering increased versatility for harnessing compressed gas cartridges of differing capacities in a unique dispenser including a novel cartridge storage feature.

18 Claims, 9 Drawing Sheets

COMPRESSED GAS CARTRIDGE DISPENSING SYSTEM ALLOWING INTERCHANGEABLE USE OF DIFFERENT CAPACITY COMPRESSED GAS CARTRIDGES AND NOVEL STORAGE FEATURE

CROSS REFERENCE TO RELATED APPLICATIONS

This application is related to and shares the benefit of a distinctly different invention titled "High Pressure Cartridge Having a Non-Threaded Neck Capable of Fitting Within a 3/8-24 Female Thread Minor Diameter With a 16 to 40 ml Water Capacity" filed on the same date by the same inventor.

FEDERALLY SPONSORED RESEARCH OR DEVELOPMENT

Not Applicable.

MICROFICHE APPENDIX OR SEQUENCE LISTING

Not Applicable.

1. Technical Field

This invention pertains to the field of dispensers that harness hand-holdable compressed gas cartridges, particularly for use in portable tire inflation systems as well as other commercial and medical applications.

2. Background Art

This application focuses on a dispensing system but a basic understanding of the variety of types of compressed gas cartridges is essential to adequately understand the versatility of this invention.

Compressed gas cartridges contain different types of gases such as carbon dioxide, oxygen, helium, nitrogen and other gases. Many different volumes of cartridges have been produced over the years. Today, one most commonly finds $CO_2$ cartridges with gas weights of 8-gram, 12-gram, 16-gram, 25-gram and larger. Cartridges are typically made of deep drawn steel as one piece, filled with gas, and then capped. Two distinct cartridge species have evolved. The first species has no threads on the neck and is sometimes referred to as a plain neck or non-threaded. The neck diameter on non-threaded cartridges does vary. The common and inexpensive 12-gram non-threaded cartridge is utilized in air guns, paintball equipment, and soda-siphons as well as portable inflators. A 16-gram non-threaded cartridge exists that is commonly used in beer dispensing equipment. The neck diameter on this 16-gram cartridge is rather large which introduces incompatibility issues with many dispensers as will be discussed. The second cartridge species has threads formed on the cartridge neck. The neck thread on many cartridges has standardized at U.S.A. (INCH) STANDARDS 3/8-24, regardless of the cartridge capacity. Common applications utilizing the 3/8-24 threaded neck cartridges include life preservers and bicycle tire or other inflation devices as well as appliances requiring a versatile working fluid. Yet, other threaded neck ifs cartridges are manufactured with other thread sizes.

As cartridge capacities increase, cartridges typically grow in length as well as body diameter. The following specifications are taken directly from an iSi Components literature that is referenced in the application information disclosure statement and added to illustrate a general size for both cartridge species, threaded or non-threaded, allowing the reader to visualize scale. A 12-gram ($CO_2$) cartridge having a water capacity of about 14 ml measures about 82.5 mm in length and about 18.6 mm in body diameter. A 16-gram ($CO_2$) cartridge having a water capacity of about 21 ml measures about 88.5 mm in length and about 22.0 mm in body diameter. A 25-gram ($CO_2$) cartridge having a water capacity of about 33 ml measures about 105.0 mm in length and about 25.4 mm in body diameter. Engineering cartridge drawings typically allow a plus and minus tolerance window for all dimensions as well as gram weight of fill gas. In this application, all reference to cartridge capacities by weight i.e. 12-gram, 16-gram, etc. are referencing gram weight of carbon dioxide or $CO_2$.

The state of the prior art has evolved in the last few years to include several configurations for the species and capacities of compressed gas cartridges and in the dispensers that harness these cartridges.

Typically, for example, a common 12-gram carbon dioxide high-pressure cartridge having no threads on the neck can be harnessed in a dispenser utilizing a cartridge-retaining container that threads onto a dispenser containing a puncturing lance and other sealing and fluid controlling means such as U.S. Pat. No. 5,544,670, filed Dec. 15, 1993, by Phillips et, al. Traditionally, only one size of non-threaded cartridge could be lanced utilizing such a dispenser featuring a retaining container device.

The industry has seen the introduction of similar high-pressure compressed gas cartridges for use in similar dispensers that incorporate threads onto the cartridge neck rather than no threads. In this situation, a retaining container attached to the dispenser is not necessary and the compressed gas cartridge need only thread into the lance housing to safely and controllably harness the compressed gas in the cartridge. Some of the reasons contributing to the introduction of the threaded type dispensing designs incorporated smaller dispensers as well as allowing any size of compressed gas cartridge, with a similar thread, to thread into the lance housing.

A German company called SKS Metaplast GmbH manufactures another species of compressed gas cartridge dispensing system. This limited versatility dispensing system is capable of harnessing only a 16-gram non-threaded, large diameter neck cartridge. Additionally, the SKS manufactured dispenser is not compatible for harnessing the common (and inexpensive) 12-gram non-threaded cartridge nor other threaded neck cartridges that do not require a cartridge-retaining container, as is thoroughly discussed in the Detailed Description.

Concentrating on the neck thread of many 12, 16, and 25-gram compressed gas cartridges, standardized at U.S.A. (INCH) STANDARDS 3/8-24, interestingly, the minor diameter of this standardized cartridge neck thread (located typically on the dispenser) is larger than the neck diameter of the common 12-gram non-threaded compressed gas cartridge. This clearance in the bore, or minor diameter of a 3/8-24 internally threaded dispenser lance housing allows a 12-gram non-threaded (very common and inexpensive) compressed gas cartridge to be harnessed in a threaded bore with the use of a cartridge-retaining container. An example of this current art is seen on several tire inflation products and other applications manufactured by Innovations In Cycling, Inc., located in Tucson, Ariz., U.S.A. Current art with many Innovations In Cycling, Inc. products allows the use of common 12-gram non-threaded cartridges (with the aid of a cartridge-retaining container), as well as allowing 12, 16, 25-gram and other threaded cartridges to be lanced and fluidly sealed with a common dispenser.

The current invention also solves another problem not previously addressed by introducing a novel cartridge-retaining container capable of storing either a common 12-gram or a 16 to 40 ml water capacity compressed gas cartridge in an upside-down orientation while the retaining container is threaded onto the dispenser as seen in FIGS. 10–13. At the internally concave, substantially spherically contoured bottom of the cartridge-retaining container is a through-bore concentric with the container that is large enough for the neck of a compressed gas cartridge, threaded or non-threaded, to reside within the bore (e.g. a bore between 7.35 mm and 16.00 mm). This feature allows the retaining container to stow a compressed gas cartridge, saving space and offering tidy protection for a cartridge.

The current invention also solves another problem not previously addressed by introducing a novel cartridge-retaining container capable of storing either a common 12-gram or a 16 to 40 ml water capacity compressed gas cartridge in an upside-down orientation while the retaining container is threaded onto the dispenser as seen in FIGS. 10–13. At the bottom of the cartridge-retaining container is a through-bore large enough for the neck of a compressed gas cartridge, threaded or non-threaded, to reside within the bore. This feature allows the retaining container to stow a compressed gas cartridge, saving space and offering tidy protection for a cartridge.

SUMMARY OF THE INVENTION

The compressed gas cartridge dispensing system of this invention is capable of dispensing the common 12-gram non-threaded neck compressed gas cartridge as well as optionally dispensing all cartridges having a ⅜-24 neck thread. The common 12-gram non-threaded neck compressed gas cartridge fits this dispenser. The same dispensing system is also capable of dispensing a larger compressed gas cartridges with a water capacity of 16 to 40 ml having neck dimensions smaller than a ⅜-24 female thread minor diameter.

The obvious advantage to the introduced dispensing system is an added option offering increased versatility for harnessing compressed gas cartridges of differing capacities (some threaded, some non-threaded) in a unique dispenser including the novel cartridge storage feature.

BRIEF DESCRIPTION OF DRAWINGS

Further aspects of the invention and their advantages may be discerned from reading the following detailed description when taken in conjunction with the drawings in which.

DETAILED DESCRIPTION OF THE INVENTION

It is an object of this invention to claim a compressed gas cartridge dispensing system capable of dispensing the common 12-gram non-threaded neck compressed gas cartridge as well as optionally dispensing all cartridges having a ⅜-24 neck thread. Additionally, the same dispensing system is capable of harnessing larger capacity compressed gas cartridges with a water capacity of 16 to 40 ml and non-threaded neck dimensioned smaller than a ⅜-24 female thread minor diameter. The novel upside-down cartridge storage feature is another object.

Figure 1:
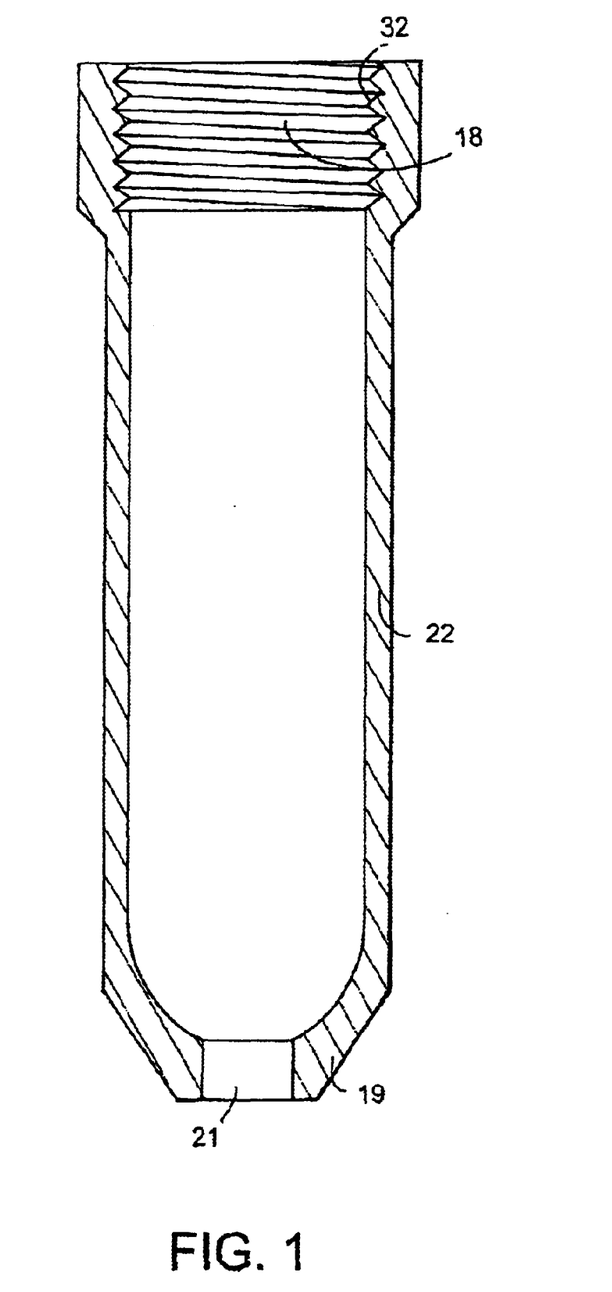
FIG. 1 is a cut-away front view of cartridge-retaining container.
Figure 6:
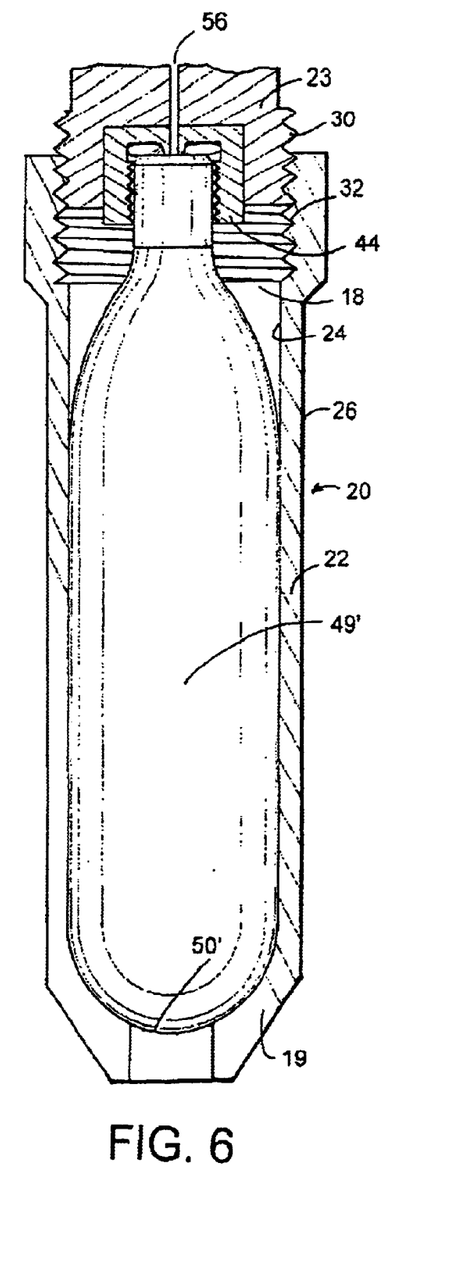
FIG. 6 is a cut-away front view of cartridge-retaining container threaded onto a dispenser. Contained in the cartridge-retaining container is a compressed gas cartridge with a water capacity of 16 to 40 ml and a non-threaded neck shown pierced by puncturing lance in internally threaded lance housing.
Figure 7:
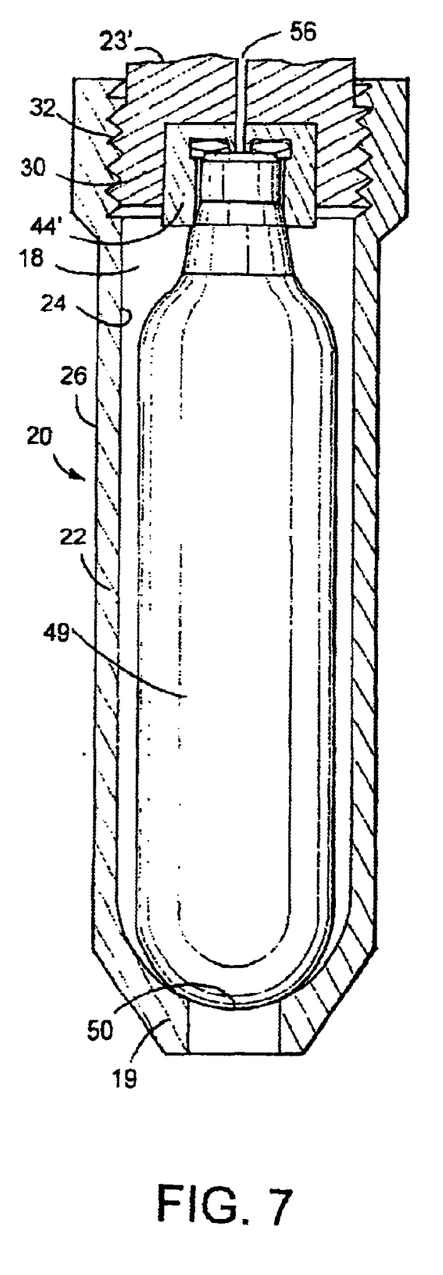
FIG. 7 is a cut-away front view of cartridge-retaining container threaded onto a dispenser. Contained in the cartridge-retaining container is a common non-threaded neck 12-gram compressed gas cartridge shown pierced by puncturing lance in an internally threaded lance housing.

FIG. 1 is a front view of cartridge-retaining container 22. Cartridge-retaining container 22 is preferably molded from a lightweight, hard yet durable plastic such as a plastic containing glass filled nylon filaments. Naturally, other materials having the afore-mentioned characteristics are similarly suitable for forming the cartridge-retaining container. Novel features of this container are the inner dimensions allowing interchangeability of the standard 12-gram non-threaded compressed gas cartridge 49 as well as allowing adequate clearance for a compressed gas cartridge with a water capacity of 16 to 40 ml and non-threaded neck 49 (FIGS. 6 and 7 show the dispenser assembled with both sizes of cartridges). An additional novel feature of this container is the ability to thread onto a dispenser (lancing head) with enough threadable range capable of adequately containing and harnessing the standard 12-gram cartridge and additionally capable of containing and harnessing the larger capacity cartridges in the range of 16 to 40 ml water capacity. Current art only offers a dispensing system dimensioned to hold the 12-gram non-threaded cartridge or only the 16-gram non-threaded cartridge. The currently available 16-gram non-threaded neck compressed gas cartridge unfortunately has a neck diameter that exceeds the minor diameter of a ⅜-24 female thread. A company called SKS Metaplast GmbH, of Germany, manufactures this limited versatility compressed gas cartridge dispensing system capable of harnessing only a 16-gram non-threaded (large diameter neck) cartridge. The SKS system is not, compatible for harnessing the common 12-gram non-threaded cartridge nor other threaded neck cartridges that do not require a cartridge-retaining container, particularly cartridges having a ⅜-24 neck thread. Due to the large loading bore, bigger than a ⅜-24 female thread minor diameter, about the SKS brand piercing lance, for accepting the large diameter neck 16-gram non-threaded cartridge; in no physical way can the same dispenser lance-locating bore have a U.S.A. (INCH) STANDARDS ⅜-24 female thread. The current invention allows expanded compatibility to harness any capacity threaded (⅜-24) cartridges not requiring a cartridge-retaining container and harnessing compatibility with different capacity cartridges having a neck diameter smaller than a ⅜-24 female thread minor diameter.

Figure 2:
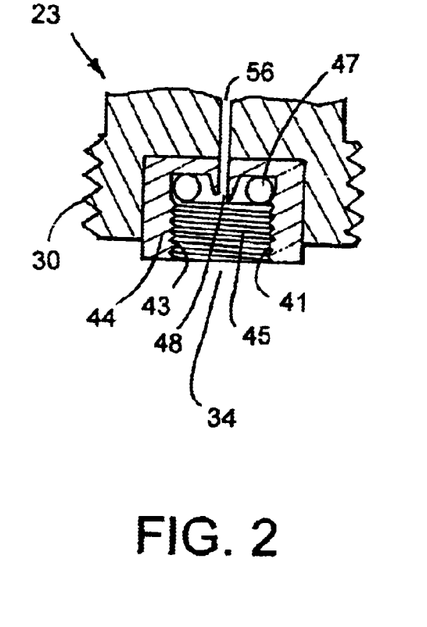
FIG. 2 is a cut-away front view of dispenser with internally threaded lance housing.
Figure 3:
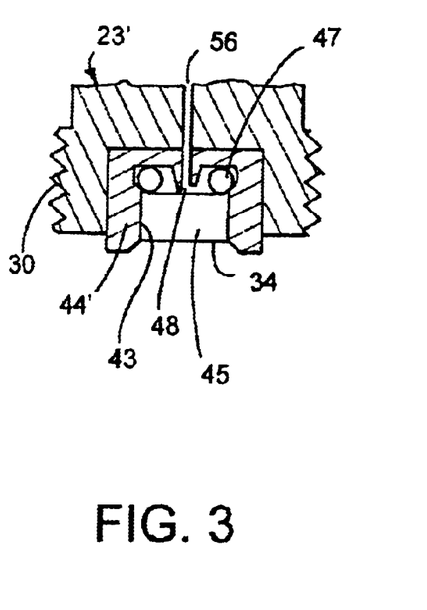
FIG. 3 is a cut-away front view of dispenser with non-internally threaded lance housing.

Referencing FIGS. 2 and 3, dispensers 23 and 23' include an opening at 34. Because many common compressed gas cartridges are commonly available with a threaded neck, the industry has evolved to include threads 41 in the lance housing 44 (FIG. 2). The purpose of the internally threaded lance housing 44 is to allow compressed gas cartridges of any volume with similar threads to thread into the dispenser 23 without the need for a cartridge-retaining container 22. The industry currently sees non-threaded lance housings 44' (FIG. 3, designated as dispenser 23') as well as threaded lance housings 44 (FIG. 2); therefore, the need exists for both designs to be mentioned.

The obvious question arises: Why even use a cartridge-retaining container to harness non-threaded compressed gas cartridges when threaded neck compressed gas cartridges are available and can be harnessed without the use of such a retaining container? The most obvious answer is cost and the other is additional versatility. Non-threaded compressed gas cartridges are typically much less expensive to manufacture. In fact, the 16-gram non-threaded compressed gas cartridge ranks as one of the least expensive cartridges, per gram of $CO_2$ to manufacture.

Continuing with FIGS. 2 and 3, extending from opening 34 is the lance housing 44 and 44' (threaded and non-threaded respectfully) formed from brass or similar rigid material. Lance housing 44 or 44' includes a cylindrical extension 43 that defines an interior area 45. Interior area 45 is dimensioned to receive and locate the neck of a pressurized gas cartridge. The generally cylindrical bore in the threaded lance housing of FIG. 2 has a U.S.A. (INCH) STANDARDS ⅜-24 female thread and the cylindrical bore in the non-threaded lance housing has a diameter at least equal to a U.S.A. (INCH) STANDARDS ⅜-24 female thread minor diameter and may have a diameter less than 9.50 mm and greater than or equal to 4.50 mm. Provided at the upper end of interior area 45 is a seal 47. Seal 47 creates a fluid connection between the outer seal circumferential area 54 of the end face of the puncturable end cap of the neck of the compressed gas cartridge (FIGS. 4a–d) and dispenser bore 56 when the compressed gas cartridge is loaded within the dispenser. Many seal profiles are suitable to provide such a fluid connection such as o-rings or flat seals. Disposed within interior area 45 of lance housing 44, 44' is a piercing lance 48 that pierces the end face of the puncturable end cap of a pressurized gas cartridge 54 (FIGS. 4a–d) when the same is brought into contact with the lance. Some lances include a hollow lumen and an obliquely cut piercing tip formed from a rigid material, such as steel or similar hardness material capable of piercing cartridge cap material. Other lances are designed with a solid obliquely cut piercing tip formed from the same or similar material. Prior art is successful utilizing many lance profiles.

Figure 4A:
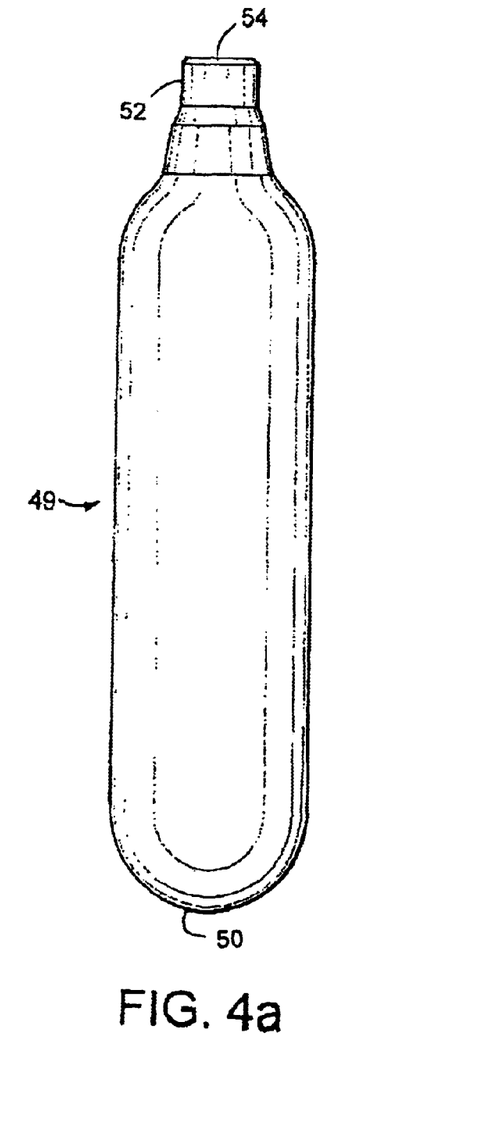
FIG. 4a shows a common 12-gram (15 ml water capacity) non-threaded or plain neck compressed gas cartridge inherently having a neck smaller than a ⅜-24 female thread minor diameter.
Figure 4B:
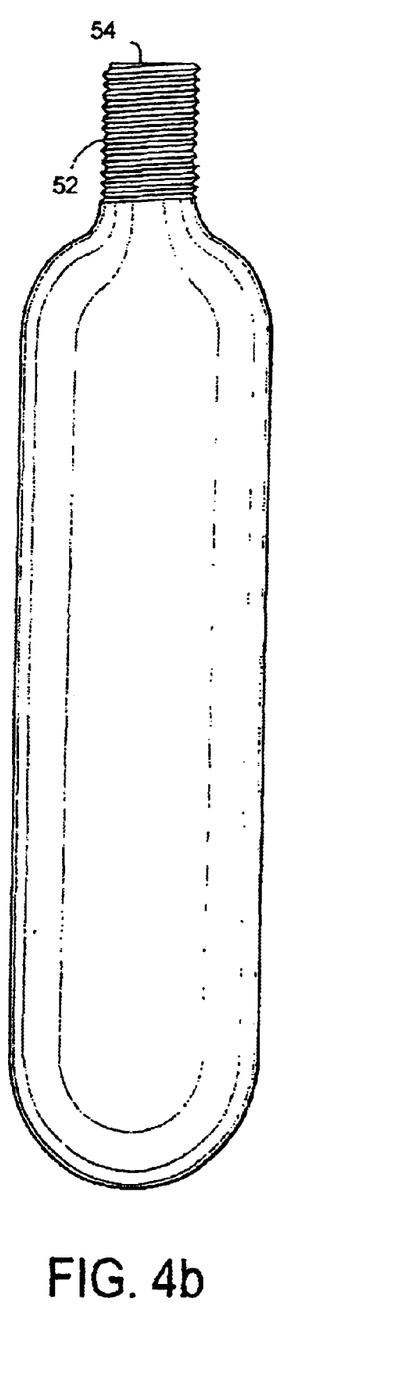
FIG. 4b shows a common 25-gram (33 ml water capacity) ⅜-24 threaded neck compressed gas cartridge.
Figure 4C:
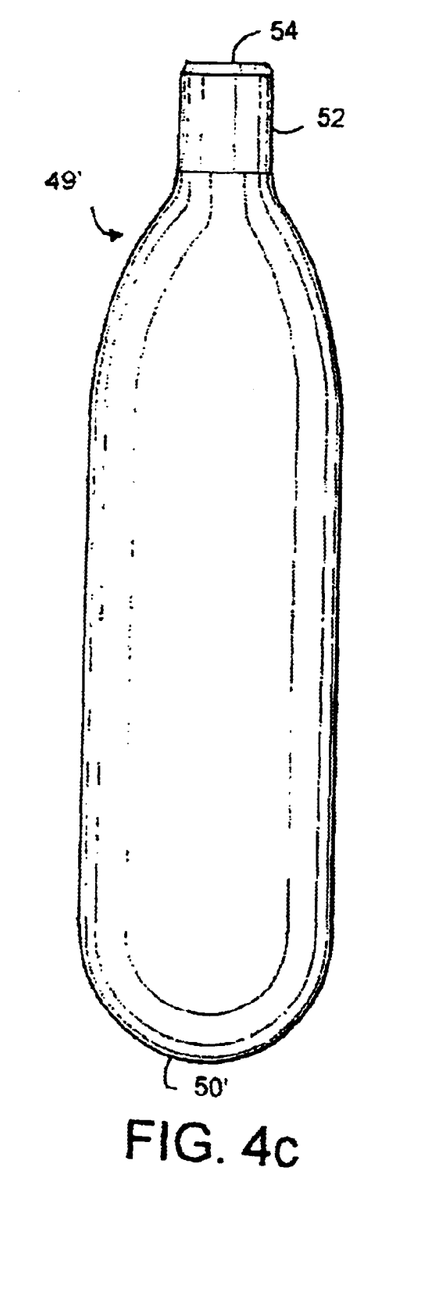
FIG. 4c shows a 16-gram (21 ml water capacity) compressed gas cartridge having a non-threaded neck diameter capable of fitting within a ⅜-24 female threaded bore. (Please see "Cross Reference to Related Applications").
Figure 4D:
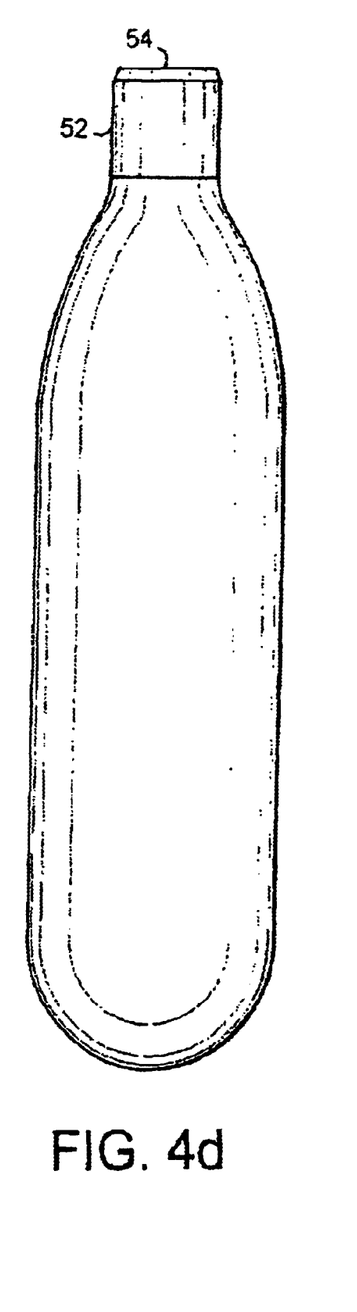
FIG. 4d shows a common 16-gram (21 ml water capacity) non-threaded neck compressed gas cartridge with neck larger than a ⅜-24 female thread minor diameter used in beer dispensers and an SKS brand inflator called the "Air Champ™, discussed in the IDS.

Referring to FIGS. 4a–d, four different compressed gas cartridges are pictured. FIG. 4a is the commonly available 12-gram non-threaded (neck) compressed gas cartridge found in common applications such as pellet guns, portable tire inflators, pneumatic wine bottle cork removers, life preservers, industrial and medical applications and the like. FIG. 4b shows a commonly available 25-gram ⅜-24 threaded neck compressed gas cartridge. FIG. 4c pictures 16-gram compressed gas cartridge having a neck smaller than a ⅜-24 female thread minor diameter for use in the multi-dispenser. FIG. 4d shows a commonly available 16 gram non-threaded neck compressed gas cartridge with a neck dimensioned larger than a ⅜-24 female thread minor diameter. Note that both species of 16-gram cartridges have substantially the same overall length and body diameter. FIG. 4c shows a 16-gram (21 ml water capacity) compressed gas cartridge that falls within the 16 to 40 water capacity range, having a neck smaller than a ⅜-24 female thread minor diameter is shown and claimed in a sister application filed on the same date by the same inventor.

Figure 5:
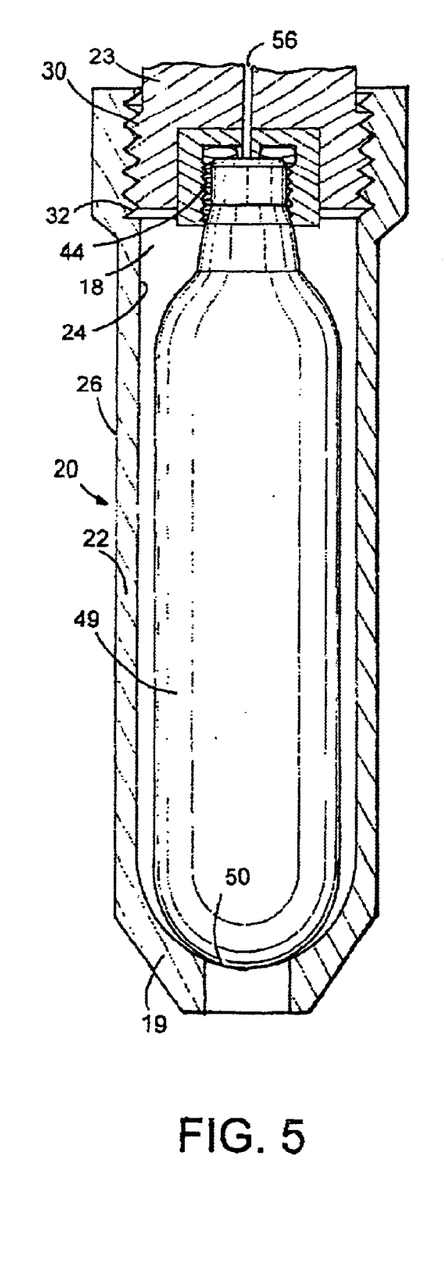
FIG. 5 is a cut-away front view of cartridge-retaining container threaded onto a dispenser. Contained in the cartridge-retaining container is a common non-threaded neck 12-gram compressed gas cartridge shown pierced by puncturing lance in an internally threaded lance housing.

FIG. 5 shows the novel internally threaded dispenser 23 piercing a standard 12-gram non-threaded compressed gas cartridge 49 with neck 52 through a ⅜-24 internally threaded lance housing 44.

FIG. 6 shows the novel internally threaded dispenser 23 piercing a preferred size 21 ml (from the preferred range of 16 to 40 ml) water capacity, non-threaded compressed as cartridge 49' with neck 52 through a ⅜-24 internally threaded lance housing 44.

FIGS. 5 and 6 have in common internally threaded lance housing 44 both utilizing an identical cartridge-retaining container 22. Note how the cartridge-retaining container to cartridge dispenser threaded connection features enough threadable range to adequately contain and pierce the standard 12-gram cartridge and additionally contain and pierce cartridges in the range of 16 to 40 ml water capacity as well as any ⅜-24 threaded neck cartridge.

FIG. 7 shows a non-internally threaded dispenser 23' piercing a standard 12-gram non-threaded compressed gas cartridge 49 containing a smooth bore lance housing 44' substantially of the same dimensions as a ⅜-24 female thread minor diameter.

Figure 8:
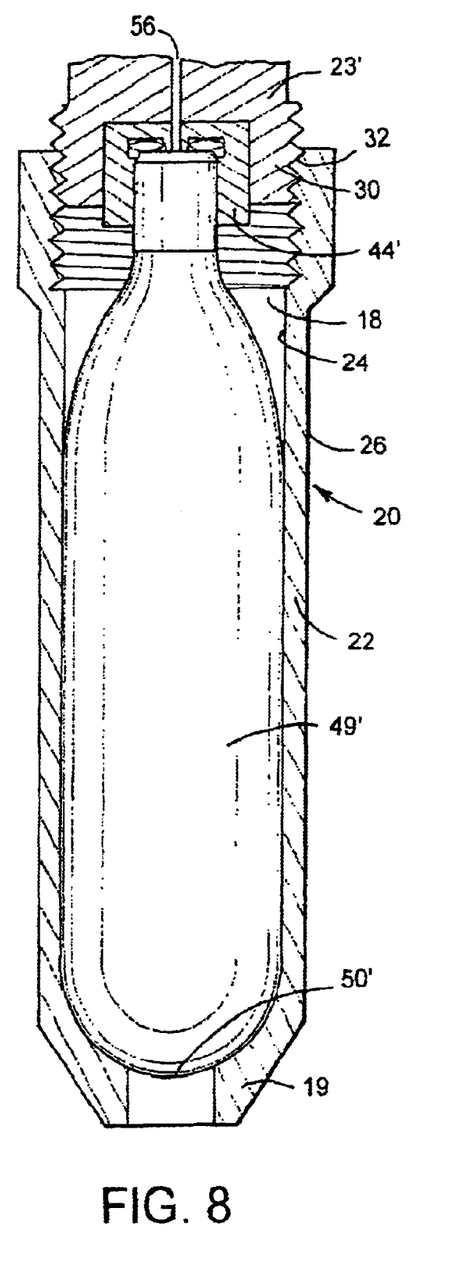
FIG. 8 is a cut-away front view of cartridge-retaining container threaded onto a dispenser. Contained in the cartridge-retaining container is a compressed gas cartridge with a water capacity of 16 to 40 ml and non-threaded neck shown pierced by puncturing lance in non-internally threaded lance housing.

FIG. 8 shows a non-internally threaded dispenser 23' piercing 21 ml water capacity (16-gram) non-threaded compressed gas cartridge 49' containing a smooth bore lance housing 44' substantially of the same dimensions as a ⅜-24 female thread minor diameter.

FIGS. 7 and 8 have in common a non-internally threaded smooth bore lance housing 44' both utilizing an identical cartridge-retaining container 22 featuring enough threadable range to adequately contain and pierce the standard 12-gram cartridge and additionally contain and pierce larger cartridges in the range of 16 to 40 ml water capacity.

Reference will be made in detail below to the preferred embodiment of the present invention as illustrated in the accompanying drawings. Referring to FIGS. 5–8, the compressed gas cartridge dispenser 20 showing cartridge-retaining container 22 is shown. The compressed gas cartridge dispenser 20 typically includes a container 22 and dispenser 23 for a threaded lance housing 44 or 23' for a non-threaded lance housing 44' capable of a variety of downstream features to control the flow of gas not pertinent to the present invention. Cartridge-retaining container 22 is preferably injection molded as one piece to form a monolithic unit formed substantially in the shape of a cylinder having an open upper end 18 and a substantially closed lower end 19. At the upper end of cartridge-retaining container 22, interior wall 24 is threaded, as at 32, to receive a correspondingly threaded portion 30 of dispenser 23, 23'. Threadably attached to cartridge-retaining container 22 is dispenser 23, 23' preferably injection molded from the same plastic used to form cartridge-retaining container 22.

The common feature that dispensers 23 and 23' (dispensers respectfully featuring threaded and non-threaded lance housings) have in common is that both designs accept the standard, inexpensive 12-gram non-threaded neck compressed gas cartridge. The industry has standardized many threaded compressed gas cartridges at U.S.A. (INCH) STANDARDS ⅜-24 thread. The minor diameter of a ⅜-24 female thread defines a clearance bore referenced in this patent. Any compressed gas cartridge having neck dimensions less than the defined ⅜-24 female thread minor diameter of any class fit is compatible with an internally threaded lance housing 44 so long as the cartridge fits within the cartridge-retaining container 22. The most common 12-gram non-threaded cartridge has a neck diameter clearly smaller than the minor diameter of a ⅜-24 female thread. This logic begs for the introduction of a larger capacity (and inexpensive) non-threaded neck compressed gas cartridge compatible with the industry standardized cartridge dispensers 20 featuring threaded and non-threaded lance housings 44, 44' within cartridge dispensers 23 and 23'.

Operation of the compressed gas cartridge dispenser 20 with a non-threaded cartridge will now be described. To insert a pressurized, non-threaded gas cartridge into the dispenser, cartridge-retaining container 22 is unscrewed from dispenser 23, 23'. A cartridge 49, 49' (FIGS. 4a,c) containing a pressurized gas inserts into the cartridge-retaining container 22 by inserting the rounded end 50, 50' of the cartridge into the cartridge-retaining container 22. Dispenser 23, 23' is mechanically connected to cartridge-retaining container 22 by threading together threaded portions 30 and 32. As dispenser 23, 23' threads into cartridge-retaining container 22, compressed gas cartridge face 54 is drawn and concentrically locates in interior area 45 of lance housing 44, 44' (FIGS. 2 and 3). As cartridge 49, 49' draws into interior area 45, a fluid connection is created between dispenser 23, 23' and cartridge 49, 49'. Careful design allows the cartridge cap 54 to contact seal 47 prior to piercing lance 48 puncturing cap 54 of cartridge 49, 49' resulting in minimized or zero loss of pressurized gas. The user continues to thread dispenser 23, 23' onto cartridge-retaining container 22 until substantial turning resistance indicates that the cartridge cap is pierced. At this point, gas flows through either hollow or around a solid piercing lance 48 downstream into bore 56 of dispenser 23, 23'. Seal 47 of lance housing 44, 44' prevents gas from leaking out from around the neck of the cartridge 49, 49' and into cartridge-retaining container 22.

Figure 9:
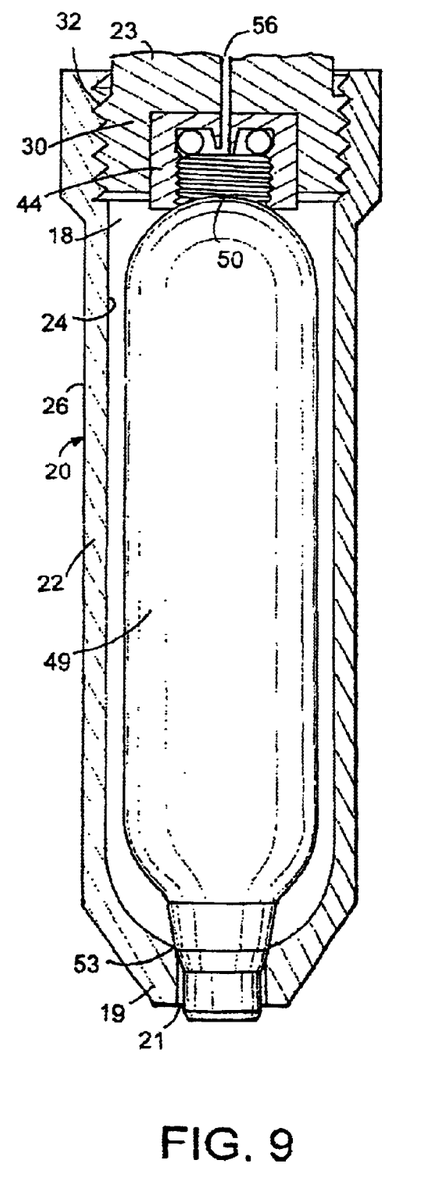
FIG. 9 is a cut-away front view of cartridge-retaining container threaded onto a dispenser featuring a threaded lance housing. Contained in the cartridge-retaining container is a common non-threaded neck 12-gram compressed gas cartridge shown stored in an upside-down orientation.
Figure 10:
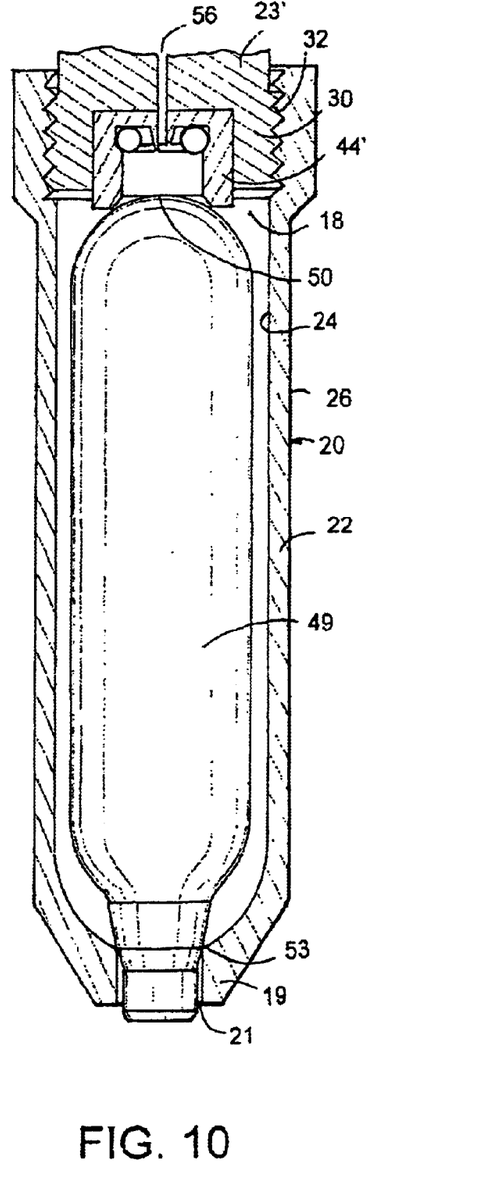
FIG. 10 is a cut-away front view of cartridge-retaining container threaded onto a dispenser featuring a non-threaded lance housing. Contained in the cartridge-retaining container is a common non-threaded neck 12-gram compressed gas cartridge shown stored in an upside-down orientation.

FIG. 9 shows the novel internally threaded dispenser 23 connectively threaded with cartridge-retaining container 22. Inside cartridge-retaining container 22 is a standard 12-gram non-threaded compressed gas cartridge 49 stowed in an upside-down orientation. The cartridge rounded end 50 circumferentially seats on the outer edge of lance-supporting member 44. Cartridge 49 additionally seats and centers by locating in cartridge-retaining container through-bore 21. The preferred bore diameter is about 9.25 mm, allowing a ⅜-24 threaded cartridge neck to protrude, but adjustment in the threadable connection 30, 32 on dispenser allows for a variety of bore diameters. FIG. 10 is similar to FIG. 9 with the difference being the dispenser 23' having a non-internally threaded smooth bore lance housing 44'. The variable range of the threadable connection 30, 32 on dispenser ensures that the claimed cartridge-retaining container 22 can threadably tighten a stowed, upside-down oriented 12-gram compressed gas cartridge 49 in the compressed gas cartridge dispenser 20.

Figure 11:
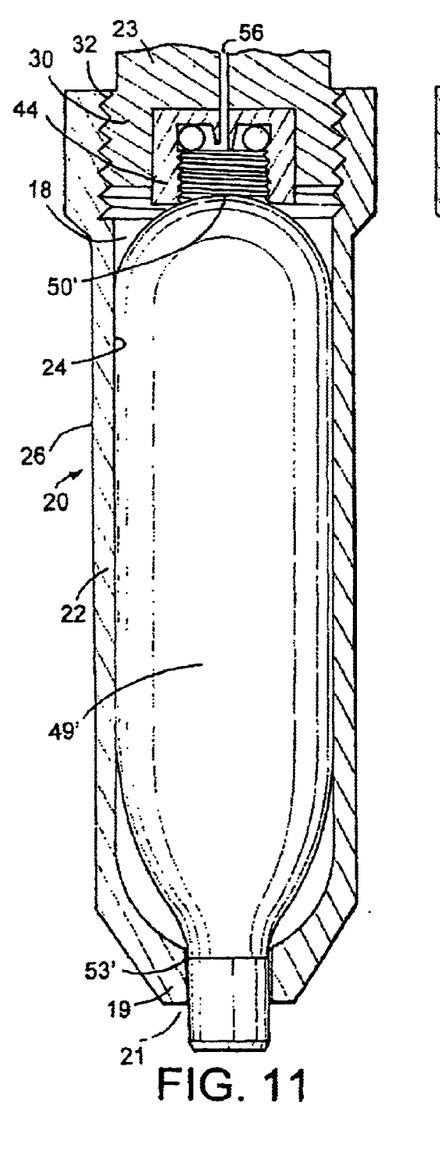
FIG. 11 is a cut-away front view of cartridge-retaining container threaded onto a dispenser featuring a threaded lance housing. Contained in the cartridge-retaining container is a compressed gas cartridge with a water capacity of 16 to 40 ml and non-threaded neck shown stored in an upside-down orientation.
Figure 12:
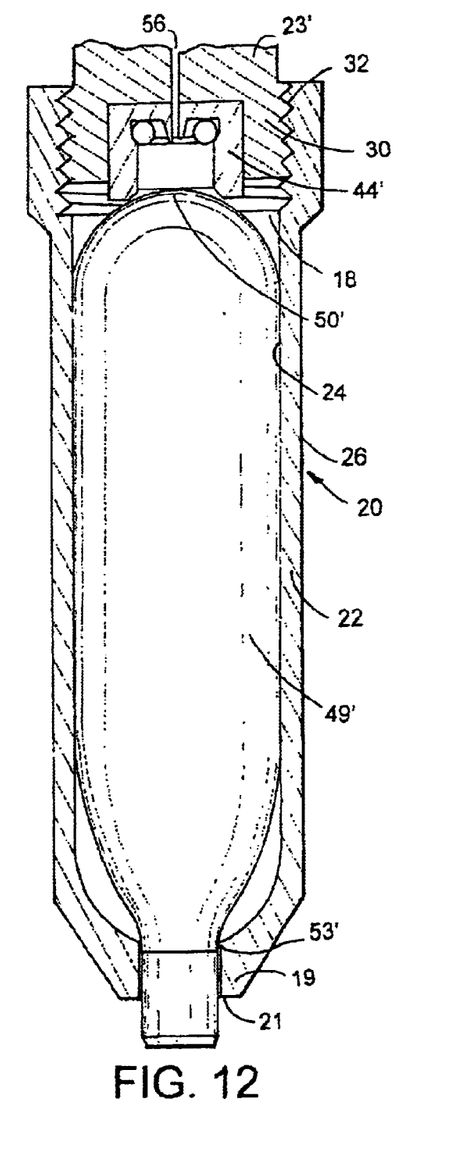
FIG. 12 is a cut-away front view of cartridge-retaining container threaded onto a dispenser featuring a non-threaded lance housing. Contained in the cartridge-retaining container is a compressed gas cartridge with a water capacity of 16 to 40 ml and non-threaded neck shown stored in an upside-down orientation.

FIG. 11 shows the novel internally threaded dispenser 23 connectively threaded with claimed cartridge-retaining container 22. Inside cartridge-retaining container 22 is the preferred size 16-gram (21 ml water capacity) non-threaded compressed gas cartridge 49' stowed in an upside-down orientation. The cartridge rounded end 50' circumferentially seats on the outer edge of lance-supporting member 44. Cartridge 49' additionally seats and centers by locating in cartridge-retaining container through-bore 21 of preferred dimensions stated in the prior paragraph. FIG. 12 is similar to FIG. 11 with the difference being the dispenser 23' having a non-internally threaded smooth bore lance housing 44'. The variable range of the threadable connection 30, 32 on dispenser ensures that the claimed cartridge-retaining container 22 can threadably tighten a stowed, upside-down oriented gas cartridge 49' with a 16 to 40 ml water capacity range.

Figure 13:
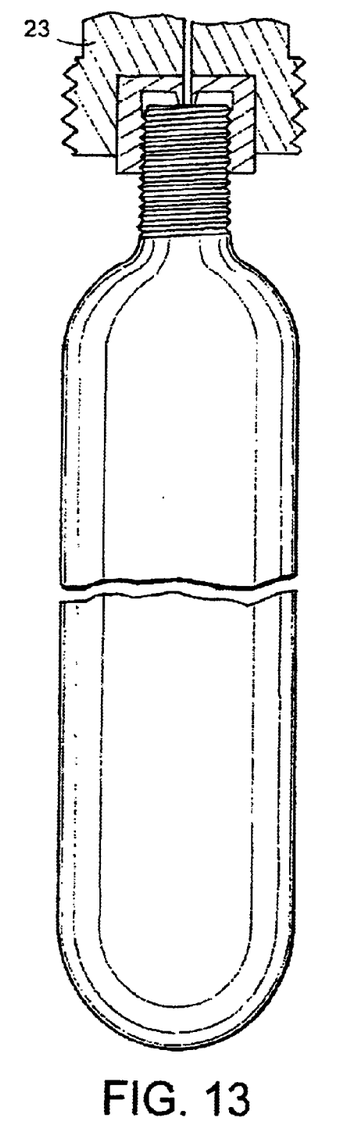
FIG. 13 shows a ⅜-24 threaded neck compressed gas cartridge lanced and fluidly sealed to cut-away view of a dispenser having a ⅜-24 internally threaded lance housing.

FIG. 13 shows an example of a compressed gas cartridge threadably connected to dispenser 23 without the need for a cartridge-retaining container.

The preferred embodiment has been disclosed in full detail. It is feasible to use an alternate mechanical means to adjust lengths of the cartridge-retaining container to allow cartridges of differing lengths to additionally be used.

I claim:

1. A compressed gas dispensing system for dispensing compressed gas from compressed gas cartridges comprising:
a dispenser means for dispensing compressed gas from any of a group of compressed gas cartridges; the compressed gas cartridges of the group each having a body having a first end with a neck that has a puncturable end cap and a second end; the group of compressed gas cartridges comprising at least two compressed gas cartridges that differ from each other in length and/or body diameter; the compressed gas cartridges of the group having capacities at least ranging from about 14 ml to about 21 ml of water; the neck of each of the compressed gas cartridges of the group having a generally cylindrical non-threaded neck portion with a maximum external diameter less than a minimum female thread minor diameter for a U.S.A. (INCH) STANDARDS ⅜-24 thread;

the dispenser means having a lance housing means; the lance housing means having a generally cylindrical bore with an open end for receiving the non-threaded neck portion of the neck of any of the compressed gas cartridges of the group and a piercing lance means within the bore for piercing the puncturable end cap of any neck of the compressed gas cartridges of the group; the bore of the lance housing means having a sealing means for forming a seal with an end face of the puncturable end cap of the neck of any of the compressed gas cartridges of the group having the puncturable end cap pierced with the piercing lance means; the bore of the lance housing means having a diameter substantially equal to a U.S.A. (INCH) STANDARDS ⅜-24 female thread minor diameter for receiving therein for lancing the non-threaded neck portion of any of the compressed gas cartridges of the group;

a cartridge retaining container means having a first bore therein for receiving any of the compressed gas cartridges of the group; the first container bore having a first open end for receiving therein the lance housing means; the first container bore having a second end; the cartridge retaining container means having end wall means at the second end of the first container bore for engaging the second end of any of the compressed gas cartridges of the group that is housed within the container means with the neck of the compressed gas cartridge within the bore of the lance housing means; and adjustable securing means for adjustably securing the cartridge retaining container means to the dispenser means for piercing the puncturable end cap of the neck of any of the compressed gas cartridges of the group received within the bore of the lance housing means by adjusting the depth to which the lance housing means extends into the cartridge retaining container means from a first depth that will pierce the puncturable end cap on a longest of the compressed gas cartridges of the group that is housed within the cartridge retaining container means to a second depth that will pierce the puncturable end cap on a shortest of the compressed gas cartridges of the group that is housed within the cartridge retaining container means.

2. The compressed gas dispensing system according to claim 1, wherein:

the end wall means at the second end of the first container bore of the cartridge retaining container means is contoured for centering any of the compressed gas cartridges of the group within the first container bore of the cartridge retaining container means.

3. The compressed gas dispensing system according to claim 1, wherein:

the adjustable securing means for adjustably securing the cartridge retaining container means to the dispenser means is also for adjusting the cartridge retaining container means relative to the lance housing means of the dispenser means so that any of compressed gas cartridges of the group can be housed within the first container bore of the cartridge retaining container means with the second end of any of the compressed gas cartridges of the group adjacent the dispenser means and the first end of any of the compressed gas cartridges of the group engaging the end wall means at the second end of the first container bore so that any of the compressed gas cartridges of the group can be stored within the cartridge retaining container means without being pierced with the piercing lance means of the lance housing means.

4. The compressed gas dispensing system according to claim 3, wherein:

the cartridge retaining container means has a second bore extending into the end wall means at the second end of the first container bore for receiving the neck of any of the compressed gas cartridges of the group stored within the cartridge retaining container means.

5. The compressed gas dispensing system according to claim 4, wherein:

the adjustable securing means for adjustably securing the cartridge retaining container means to the dispenser comprises mating threads on the dispenser means and the cartridge retaining container means.

6. The compressed gas dispensing system according to claim 1, wherein:

the adjustable securing means for adjustably securing the cartridge retaining container means to the dispenser comprises mating threads on the dispenser means and the cartridge retaining container means.

7. The compressed gas dispensing system according to claim 1, wherein:

the bore of the lance housing means is unthreaded.

8. The compressed gas dispensing system according to claim 1, wherein:

the bore of the lance housing means has a portion that is threaded with a U.S.A. (INCH) STANDARDS ⅜-24 thread so that, in addition to the compressed gas cartridges of the group, compressed gas cartridges having threaded necks that are threaded with a U.S.A. (INCH) STANDARDS ⅜-24 thread can be threaded into the bore of the lance housing to be pierced by the piercing lance means.

9. The compressed gas dispensing system according to claim 8; wherein:

the sealing means in the bore of the lance housing means for forming a seal with the puncturable end face of the neck of any of the compressed gas cartridges of the group having the puncturable end cap pierced with the piercing lance means is an O-ring.

10. The compressed gas dispensing system according to claim 9, wherein:

the adjustable securing means for adjustably securing the cartridge retaining container means to the dispenser comprises mating threads on the dispenser means and the cartridge retaining container means.

11. The compressed gas dispensing system according to claim 8, wherein:

the end wall means at the second end of the first container bore of the cartridge retaining container means is contoured for centering any of the compressed gas cartridges of the group within the first container bore of the cartridge retaining container means.

12. The compressed gas dispensing system according to claim 8, wherein:

the adjustable securing means for adjustably securing the cartridge retaining container means to the dispenser means is also for adjusting the cartridge retaining container means relative to the lance housing means of the dispenser means so that any of compressed gas cartridges of the group can be housed within the first container bore of the cartridge retaining container means with the second end of any of the compressed gas cartridges of the group engaging the lance housing means and the first end of any of the compressed gas cartridges of the group engaging the end wall means at the second end of the first container bore so that any of the compressed gas cartridges of the group can be stored within the cartridge retaining container means without being pierced with the piercing lance d the lance housing means.

13. The compressed gas dispensing system according to claim 12, wherein:

the cartridge retaining container means has a second bore extending into the end wall means at the second end of the first container bore for receiving the neck of any of the compressed gas cartridges of the group stored within the cartridge retaining container means.

14. The compressed gas dispensing system according to claim 8, wherein:

the adjustable securing means for adjustably securing the cartridge retaining container means to the dispenser means comprises mating threads on the dispenser means and the cartridge retaining container means.

15. The compressed gas dispensing system according to claim 1, wherein:

the compressed gas cartridges of the group have capacities at least ranging from about 14 ml to about 33 ml of water.

16. The compressed gas dispensing system according to claim 1, wherein:

the group of compressed gas cartridges comprises at least three compressed gas cartridges that differ from each other in length and/or body diameter, and the compressed gas cartridges of the group have capacities at least ranging from about 14 ml to about 33 ml of water.

17. The compressed gas dispensing system according to claim 1, wherein:

the compressed gas cartridges of the group have capacities at least ranging from about 14 ml to about 40 ml of water.

18. The compressed gas dispensing system according to claim 1, wherein:

the compressed gas cartridges of the group have capacities at least ranging from about 14 ml to about 50 ml of water.

* * * * *